United States Patent
Kim et al.

(10) Patent No.: US 6,911,152 B2
(45) Date of Patent: Jun. 28, 2005

(54) HIGH-SENSITIVITY METHOD AND APPARATUS FOR MONITORING IMPURITIES IN WATER

(75) Inventors: Woo-young Kim, Seoul (KR); Tae-won Lee, Daejeon-shi (KR); Jeom-in Baek, Daejeon-shi (KR); Yu-chan Yoon, Daejeon-shi (KR); Seung-min Lee, Daejeon-shi (KR)

(73) Assignee: Korea Electric Power Corporation, Seoul (KR)

( * ) Notice: Subject to any disclaimer, the term of this patent is extended or adjusted under 35 U.S.C. 154(b) by 42 days.

(21) Appl. No.: 10/234,712

(22) Filed: Sep. 5, 2002

(65) Prior Publication Data

US 2003/0080063 A1 May 1, 2003

(30) Foreign Application Priority Data

Oct. 25, 2001 (KR) ........................................ 2001-66088

(51) Int. Cl.$^7$ ............................. C02F 1/42; B01D 35/14
(52) U.S. Cl. ........................................ 210/662; 210/85
(58) Field of Search ................................ 210/660, 662, 210/85

(56) References Cited

U.S. PATENT DOCUMENTS 4,219,413 A * 8/1980 Jackson et al. ............. 210/662

FOREIGN PATENT DOCUMENTS

JP 08155451 A * 6/1996

* cited by examiner

*Primary Examiner*—Robert A. Hopkins
(74) *Attorney, Agent, or Firm*—Shlesinger, Arkwright & Garvey LLP

(57) ABSTRACT

Disclosed herein are a high-sensitivity method and apparatus for monitoring the concentration or inflow of impurities in circulating water of a circulating water system, which can remarkably improve the measurement sensitivity by converting carbonate ions of low conductivity into chlorine or sulfate ions of increased conductivity, and which can measure the inflow of air or organic substances and the amount of inflow in a simple and efficient manner in real-time. The method of the present invention comprises the steps of: increasing a content of strong acids in sample water and thus increasing equivalent conductivity of the impurities, by utilizing cation exchange resin together with anion exchange resin, in which cations of the sample water are adsorbed on the cation exchange resin to form strong acids while weakly acidic anions of low dissociation degree in the sample water are adsorbed on the anion exchange resin to form strong acids; and measuring the increased conductivity of the impurities.

8 Claims, 2 Drawing Sheets

- PRIOR ART -

HIGH-SENSITIVITY METHOD AND APPARATUS FOR MONITORING IMPURITIES IN WATER

BACKGROUND OF THE INVENTION

1. Field of the Invention

The present invention relates to a method and apparatus for monitoring cationic conductivity, which are used to sense the concentration or inflow of impurities in circulating water of a circulating water system. More particularly, the present invention relates to an improved method which remarkably improves the measurement sensitivity for cationic conductivity by utilizing a mixed-type column where cation exchange resin and anion exchange resin are present together, and also permits an apparatus to carry out the same.

2. Background of the Related Art

Generally, impurities (salts) in water consist of cations including sodium, calcium and magnesium, and anions including sulfate ion and carbonate ion. An increase in concentration of impurities in system circulation water results in acceleration of corrosion or production of scales, thereby reducing equipment lifespan and lowering heat efficiency. For this reason, concentration of the impurities in water needs to be maintained at low level. In most industrial fields, industrial water containing large amounts of the impurities is used as cooling water for a heat exchanger. Thus, if fine holes caused by corrosion, etc. are formed on a cooling tube, the impurities are introduced or concentrated in the system so that concentration of the impurities is liable to increase. For this reason, the construction of a system for regularly monitoring the impurities in water is very critical.

A conventional method and apparatus for measuring cationic conductivity, which are most generally used for monitoring impurities in water, will now be described with reference to FIG. 1. In such a method for measuring the cationic conductivity, sample water 1 is passed into a column filled with a cation exchange resin via a valve 2 and a flow meter 3, so that cations (e.g., $Na^+$) constituting the impurities in the sample water 1 is converted into hydrogen ions ($H^+$), and anions of the impurities remain intact and are finally converted into hydrochloric acid (HCl), thereby highly increasing conductivity of the impurities. The increased conductivity is measured by a measuring unit comprising an electrode 5 and an indicator 5, whereby impurities are detected.

Table 1 below shows equivalent conductivity of anions and cations which are generally present in water. For example, where water containing salts (NaCl) is introduced and passed through a cation exchange column, sodium ions (equivalent conductivity: 50.1) as cations are substituted with hydrogen ions (equivalent conductivity: 49.8), thereby highly increasing conductivity of the impurities. Namely, according to reaction represented by the following reaction equation, the equivalent conductivity before passage through the cation exchange column is 126.45 (50.1+76.35) but the equivalent conductivity after passage through the cation exchange column is 426.15 (349.8+76.35).

$Na^+ + Cl^- + R$—H (hydrogen-type cation exchange resin)→$H^+ + Cl^- + R$—Na Thus, as conductivity the impurities is highly increased, a content of impurities can be easily detected by measuring an increase in conductivity.

TABLE 1

Equivalent Conductivities of Various Ions (mho · $cm^2$ · $eq^2$) at 25° C.

| Cations | Equivalent conductivity | Anions | Equivalent conductivity |
| --- | --- | --- | --- |
| $Na+$ | 50.1 | $Cl^-$ | 76.35 |
| $Ca^{2+}$ | 59.5 | $SO_4^{2-}$ | 80.02 |
| $H^+$ | 349.8 | $CO_3^{2-}$ | 69.3 |
| $NH_4^+$ | 73.55 | $HCO_3^-$ | 44.5 |

Generally, seawater contains anions in the order of chlorine ions, sulfate ions and carbonate ions in amount, and freshwater contains anions in the order of carbonate ions, chlorine ions and sulfate ions in amount. Where sample water is passed through the cation exchange column, cations in impurities are substituted with hydrogen ions, so that chlorine ions, sulfate ions and carbonate ions (or bicarbonate ions) are converted into hydrochloric acid, sulfuric acid and carbonic acid, respectively.

As indicated in Table 2 below, hydrochloric acid and sulfuric acid, that are strong acids, are nearly completely dissociated due to their high dissociation degree and thus contribute to increasing conductivity of the impurities. However, since carbonic acid, that is a weak acid, very partially contributes to increasing conductivity of the impurities, it shows low conductivity even when it is present in water at high concentration.

TABLE 2

Dissociation Constant of Various Acids

| Acids | Chemical formula | Dissociation constant |
| --- | --- | --- |
| Hydrochloric acid | HCl | $1.26 \times 10^5$ |
| Sulfuric acid | $H_2SO_4$ | $10^3$ |
| Carbonic acid | $H_2CO_3$ | $4.3 \times 10^{-7}$ |
| Phosphoric acid | $H_3PO_4$ | $7.5 \times 10^{-3}$ |
| Fluoric acid | HF | $2.7 \times 10^{-2}$ |

Seawater contains the impurities at a relatively high concentration so that the impurities can be easily detected even when they are introduced at a very small amount. However, freshwater contains the impurities at a relatively low amount. Thus, where cooling water is introduced into a system in an industrial field using freshwater as cooling water (e.g., cogeneration power plant), it is disadvantageous in that monitoring of the inflow of cooling water is difficult due to its low detection sensitivity even when the measurement of conductivity is carried out using the cation exchange column.

Furthermore, in a method for monitoring the inflow of air or organic substances into a system according to the present invention, conductivity of water effluent from the cation exchange column is measured for detection of carbon dioxide (about 350 ppm) present in air or for detection of carbon dioxide produced by decomposition of organic substances. Then, the effluent water is heated to the boiling point to remove carbonate ions, after which conductivity of water is measured again. From a difference between the two measured conductivities, concentration of carbonate ions is measured. However, this method has problems in that it is complicated and real-time measurement is made impossible.

SUMMARY OF THE INVENTION

Accordingly, a first object of the present invention is to provide a method for measuring cationic conductivity, which can efficiently sense the inflow of cooling water into a system at high sensitivity even when freshwater is used as the cooling water.

A second object of the present invention is to provide a method for measuring cationic conductivity, which can sense an increase in carbonic ion concentration caused by the inflow of air or organic substances into a system, in a simple and efficient manner in real-time.

A third object of the present invention is to provide an apparatus for measuring cationic conductivity, which allows achieving the first and second objects, in an efficient and smooth manner.

According to a preferred aspect of the present invention for achieving the first object of the present invention, there is provided a high-sensitivity method for monitoring impurities in water, which comprises the steps of: increasing a content of strong acids in sample water and thus increasing equivalent conductivity of the impurities, by utilizing cation exchange resin together with anion exchange resin, in which cations of the sample water are adsorbed on the cation exchange resin to form strong acids while weakly acidic anions of low dissociation degree in the sample water are adsorbed on the anion exchange resin to form strong acids; and measuring the increased conductivity of the impurities.

According to a preferred aspect of the present invention for achieving the second object of the present invention, there is provided a high-sensitivity method for monitoring impurities in water, which comprises the steps of: exchanging cations of sample water by passing the sample water through a cation exchange resin column, so that the cations are adsorbed so as to form strong acids of high dissociation degree; measuring conductivity of the sample water from the cation exchange resin column; exchanging anions of the sample water by passing the sample water from the cation exchange resin column through an anion exchange resin column, so that the anions of the sample water are adsorbed to form strong acids of high dissociation degree; measuring conductivity of the sample water from the anion exchange resin column; and measuring concentration of weak acids of low dissociation degree in the sample water, from a difference between the measured conductivity value for the sample water passed through the cation exchange resin column and the measured conductivity value for the sample water passed through the anion exchange resin column.

According to a preferred aspect of the present invention for achieving the third object of the present invention, there is provided a high-sensitivity apparatus for monitoring impurities in water, which comprises a mixed-type column filled with cation exchange resin and anion exchange resin where the cation exchange resin and the anion exchange resin are present together; and a measuring unit for measuring and indicating conductivity of water, the measuring unit comprising an electrode and an indicator.

According to a preferred aspect of the present invention for achieving the third object of the present invention, there is provided a high-sensitivity apparatus for monitoring impurities in water, which comprises a cation exchange resin column; an anion exchange resin column disposed following the cation exchange resin column; and a measuring unit for measuring and indicating conductivity of water, the measuring unit comprising an electrode and an indicator.

It is to be understood that both the foregoing general description and the following detailed description of the present invention are exemplary and explanatory and are intended to provide further explanation of the invention as claimed.

BRIEF DESCRIPTION OF THE DRAWINGS

The above and other objects, features and advantages of the present invention will be apparent from the following detailed description of the preferred embodiments of the invention in conjunction with the accompanying drawings, in which.

DETAILED DESCRIPTION OF THE PREFERRED EMBODIMENT

Reference will now be made in detail to the preferred embodiments of the present invention.

Sample water to be measured, such as system water or cooling water of industrial equipment is passed through a column filled with cation exchange resin, so that cations that constitute impurities in the sample water, including $Na^+$, $Ca^{2+}$ and $Mg^{2+}$, are exchanged with, for example, $H^+$ ions. At the same time, the released $H^+$ ion is bound with anions remaining intact, such as $Cl^-$ and $SO_4^{2-}$, to form acids of high dissociation degree, so that conductivity of the impurities is relatively increased. An increase in conductivity value of the impurities allows detection of the inflow of impurities into a system and the amount of inflow of impurities.

The sample water passed through the cation exchange resin column is passed through a column filled with anion exchange resin, so that weakly acidic anions in the sample water, such as carbonate ions or phosphate ions, are exchanged with $Cl^-$ ions to form HCl. Thus, since conductivity of the impurities is relatively increased, a very small amount of the impurities can be also detected in an easy and efficient manner. The anion exchange column which can be used in the practice of the present invention is preferably a chlorine-type in terms of the improvement of sensitivity.

By using the anion exchange resin as described above, anions such as carbonate ions or phosphate ions are substituted with chlorine ions, so that equivalent conductivity of the impurities (or cooling water) is increased. Thus, the inflow of impurities into a system and the amount of inflow of impurities can be sensed in a simple and efficient manner.

In the prior art, for example, carbonate ions which had hardly contributed to an increase in conductivity of the impurities were substituted with chlorine ions according to reaction represented by the following reaction equation, so that it could exhibit high conductivity:

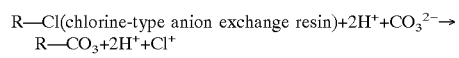

R—Cl(chlorine-type anion exchange resin)+$2H^+$+$CO_3^{2-}$ → R—$CO_3$+$2H^+$+$Cl^+$ In the case as described above, it is understood that, when performance of the anion exchange column becomes exhausted, it is regenerated with salt or hydrochloric acid, so that chlorine ions are adsorbed on the anion exchange resin according to the following equation and carbonate ions are desorbed, whereby the anion exchange column can be continuously used:

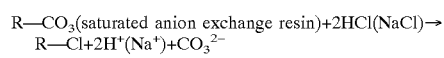

Figure 1:
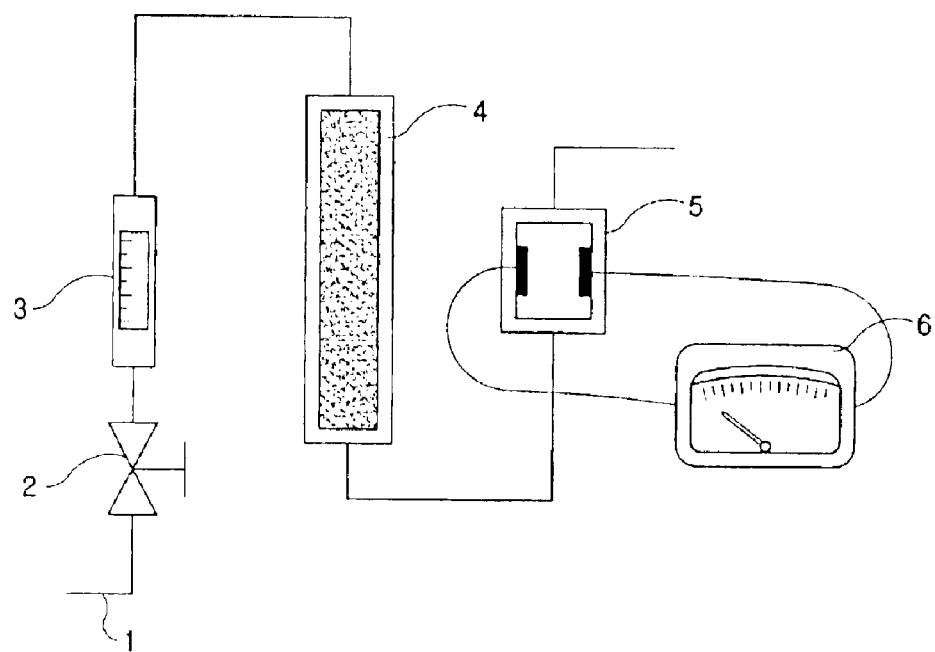
FIG. 1 schematically shows an apparatus for measuring cationic conductivity according to the prior art.
Figure 2:
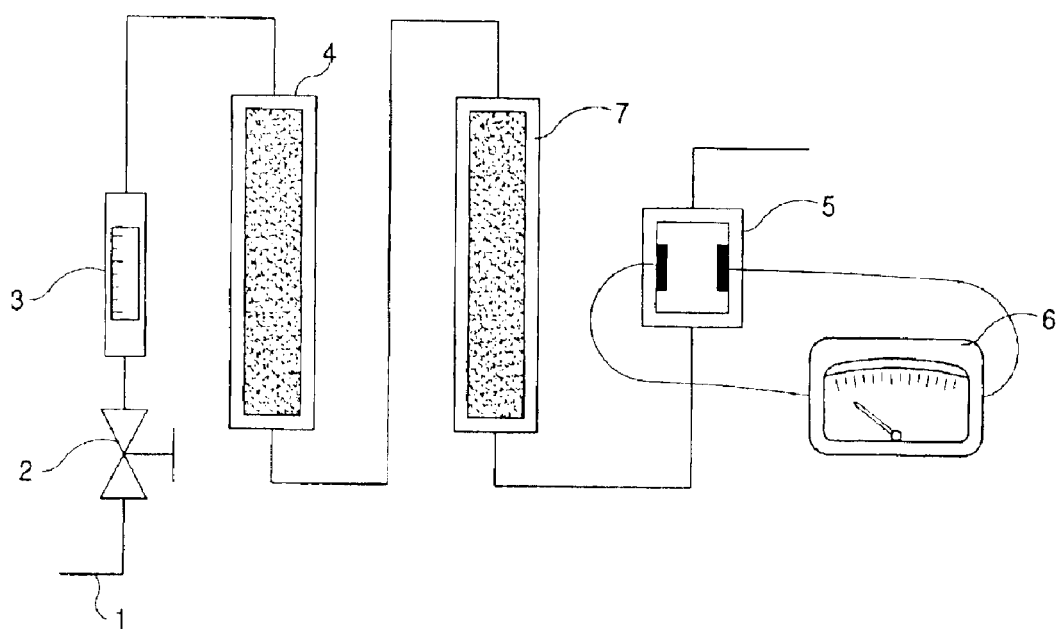
FIG. 2 schematically shows an apparatus for measuring cationic conductivity according to the present invention.

R—$CO_3$(saturated anion exchange resin)+2HCl(NaCl)→ R—Cl+$2H^+(Na^+)$+$CO_3^{2-}$ FIG. 2 schematically shows a high-sensitivity apparatus for monitoring impurities in water, which is used for conducting the high-sensitivity method for monitoring impurities in water according to the present invention in a smooth and efficient manner. In the apparatus shown in FIG. 2, a valve 2 connected to a circulating water system (system where clean water is circulated) is controlled, such that sample water 1 flows through a flow meter 3 at a predetermined flow rate. The sample water 1 is passed through a cation exchange column 4 and then an anion exchange column 7, and discharged to the outside via an electrode 5. Conductivity of the sample water is indicated in real-time at a measuring meter 6. Since conductivity of the impurities varies depending on flow rate and temperature of the sample water, flow rate and temperature of the sample water need to be maintained at a constant level.

In addition to the method and apparatus as described above, a mixed-type single column where the cation exchange resin and the anion exchange resin are present together can be also used to carry out the method of the present invention. It is to be understood that the use of the mixed-type single column is within the scope of the present invention.

The present invention will hereinafter be described in further detail by examples. It should however be borne in mind that the present invention is not limited to or by the examples.

EXAMPLE 1

Tap Water as Freshwater

In an application example, 5 ml of tap water was taken in a beaker and diluted with pure water to have a volume of 2,000 ml. At this time, this diluted water exhibited a measured conductivity of 1.277 $\mu$S/cm. After passage through a hydrogen-type cation exchange column, the diluted water exhibited a measured conductivity of 3.24 $\mu$S/cm which corresponds to an increase of 154% as compared with before passage through the cation exchange column. After passage through a chlorine-type anion exchange column, the diluted water exhibited a measured conductivity of 4.65 $\mu$S/cm which corresponds to an increase of 272% as compared with before passage through the cation exchange column and an increase of 44% after passage through the cation exchange column.

As a result, even though the amount of inflow of impurities into a system is constant, the use of the method and apparatus according to the present invention permits detection of the inflow of impurities at a far higher sensitivity. Thus, it is expected that, even when cooling water containing impurities is introduced at a small amount, the method and apparatus of the present invention allows sensing the impurities and thus can contribute to maintain a healthy property of the system.

EXAMPLE 2

Seawater 1.1 ml of seawater (natural seawater) was diluted with pure water to have a volume of 2 liters, and the diluted water exhibited a measured conductivity of 5.6 $\mu$S/cm. After passage through a hydrogen-type cation exchange column, the diluted water exhibited a measured conductivity of 11.45 $\mu$S/cm which corresponds to an increase of 101% as compared with before passage through the cation exchange column. After passage through a chlorine-type anion exchange column, the diluted water exhibited a measured conductivity of 15.6 $\mu$S/cm which corresponds to an increase of 179% as compared with before passage through the cation exchange column and an increase of 36% after passage through the cation exchange column.

EXAMPLE 3

Water Containing Sodium Carbonate Dissolved Therein

A predetermined amount of a 0.1N sodium carbonate ($Na_2CO_3$) solution was added to pure water, and the sodium-carbonate-containing water exhibited a measured conductivity of 54.9 $\mu$S/cm. After passage through a hydrogen-type cation exchange column, the sodium carbonate-containing water exhibited a measured conductivity of 6.73 $\mu$S/cm which corresponds to a reduction of 87% as compared with before passage through the hydrogen-type cation exchange column. This is because sodium carbonate was converted into carbonic acid ($H_2CO_3$) which shows a dissociation degree lower than sodium carbonate. After passage through a chlorine-type anion exchange column, the water exhibited a measured conductivity of 47.6 $\mu$S/cm which corresponds to an increase of 904% as compared with after passage through the cation exchange column.

As described above, in industrial equipment, including a thermoelectric power station, an atomic power station and semiconductor manufacturing equipment, which utilizes industrial water containing large amounts of impurities as cooling water and in which the inflow of impurities into the circulating water system must be positively inhibited, the present invention can be effectively used in establishing a suitable countermeasure at an early stage by detecting even the inflow of impurities of a small amount at a high sensitivity. In particularly, where freshwater is used as cooling water, the present invention permits remarkable improvement in the measurement sensitivity in the range of about 40 to 200% depending on the composition of impurities in water, since carbonate ions is contained in water at a larger amount than chlorine ions or sulfate ions. This makes monitoring of impurity inflow easy as compared with the prior art. Furthermore, in the prior art, in order to automatically measure concentration of carbonate ions in water, sample water is boiled to the boiling point to remove the carbonate ions and are then measured for conductivity, but the use of the method according to the present invention advantageously makes possible real-time measurement without heating.

The forgoing embodiments are merely exemplary and are not to be construed as limiting the present invention. The present teachings can be readily applied to other types of apparatuses. The description of the present invention is intended to be illustrative, and not to limit the scope of the claims. Many alternatives, modifications, and variations will be apparent to those skilled in the art.

What is claimed is:

1. A high-sensitivity method for monitoring impurities in water, consisting essentially of the steps of:

a) increasing a content of strong acids in sample water and thus increasing equivalent conductivity of the impurities, by utilizing a hydrogen-type cation exchange resin together with a chlorine-type anion exchange resin, in which cations of the sample water are adsorbed on the cation exchange resin to form strong acids and then weakly acidic anions of low dissociation degree in the sample water are adsorbed on the anion exchange resin to form strong acids, the sample water being passed through the hydrogen-type cation exchange resin, then the sample water being passed through the chlorine-type anion exchange resin; and then measuring the increased conductivity of the impurities in the water in real-time.

2. A high-sensitivity method for monitoring impurities in water, which comprises the steps of:
   a) exchanging cations of sample water by passing the sample water through a hydrogen-type cation exchange resin column, so that the cations are adsorbed so as to form strong acids of high dissociation degree;
   b) measuring conductivity of the sample water from the cation exchange resin column;
   c) exchanging anions of the sample water by passing the sample water from the cation exchange resin column through an anion exchange resin column, so that the anions of the sample water are adsorbed to form strong acids of high dissociation degree;
   d) measuring conductivity of the sample water from the anion exchange resin column; and
   e) measuring concentration of weak acids of low dissociation degree in the sample water, from a difference between the measured conductivity value of the sample water passed through the cation exchange resin column and the measured conductivity value for the sample water passed through the anion exchange resin column.

3. A high-sensitivity method for monitoring impurities in water as in claim 2, wherein:
   a) the anion exchange resin column includes a chlorine-type exchange column.

4. A high-sensitivity method for monitoring impurities in water as in claim 3, wherein:
   a) the cation exchange resin column and the anion exchange resin column include a mixed-type single column.

5. A high-sensitivity method for monitoring impurities in water as in claim 3, wherein:
   a) the cation exchange resin column includes a hydrogen-type cation exchange resin.

6. A high-sensitivity method for monitoring impurities in water as in claim 2, wherein:
   a) the cation exchange resin column includes a hydrogen-type cation exchange resin.

7. A high-sensitivity apparatus for monitoring impurities in water, consists essentially of:
   a) a mixed-type column filled with hydrogen-type cation exchange resin and chlorine-type anion exchange resin, where the cation exchange resin and the anion exchange resin are present together; and
   b) a measuring unit for measuring and indicating conductivity of water, the measuring unit comprising an electrode and an indicator.

8. A high-sensitivity apparatus for monitoring impurities in water, consisting essentially of:
   a) a hydrogen-type cation exchange resin column;
   b) a chlorine-type anion exchange resin column fluidly connected to and disposed following the cation exchange resin column, the anion exchange resin column receiving water from the cation exchange resin column, in use; and
   c) a measuring unit for measuring and indicating conductivity of water, the measuring unit comprising an electrode and an indicator, and the measuring unit being disposed for measuring and indicating conductivity of water which has passed through the the cation exchange resin column and the anion exchange resin column, in use.

* * * * *